US012662454B2

(12) United States Patent
Baati et al.

(10) Patent No.: US 12,662,454 B2
(45) Date of Patent: Jun. 23, 2026

(54) HYDROXY-PYRIDINALDOXIME SCAFFOLDS

(71) Applicants: CENTRE NATIONAL DE LA RECHERCHE SCIENTIFIQUE, Paris (FR); ETAT FRANçAIS, SERVICE DE SANTÉ DES ARMÉES REPRÉSÉNTÉ PAR LE DÉLÉGUÉ GÉNÉRAL DE L'ARMEMENT, Paris (FR); UNIVERSITÉ DE STRASBOURG, Strasbourg (FR)

(72) Inventors: Rachid Baati, Strasbourg Cedex (FR); Richard Brown, Hampshire (GB); José Dias, Brétigny sur Orge (FR); Alex Maryan-Instone, Southampton (GB); Florian Nachon, Bretigney sur Orge (FR); Jagadeesh Yerri, Strasbourg Cedex (FR); Camille Voros, Strasbourg (FR)

(73) Assignees: CENTRE NATIONAL DE LA RECHERCHE SCIENTIFIQUE, Paris (FR); ETAT FRANçAIS, SERVICE DE SANTÉ DES ARMÉES REPRÉSÉNTÉ PAR LE DÉLÉGUÉ GÉNÉRAL DE L'ARMEMENT, Paris (FR); UNIVERSITÉ DE STRASBOURG, Strasbourg (FR); UNIVERSITY OF SOUTHAMPTON, Southampton (GB)

( * ) Notice: Subject to any disclaimer, the term of this patent is extended or adjusted under 35 U.S.C. 154(b) by 511 days.

(21) Appl. No.: 18/043,958

(22) PCT Filed: Sep. 9, 2021

(86) PCT No.: PCT/EP2021/074846
§ 371 (c)(1),
(2) Date: Mar. 3, 2023

(87) PCT Pub. No.: WO2022/053572
PCT Pub. Date: Mar. 17, 2022

(65) Prior Publication Data

US 2024/0025854 A1 Jan. 25, 2024

(30) Foreign Application Priority Data

Sep. 11, 2020 (EP) .................................... 20306013

(51) Int. Cl.
*C07D 213/65* (2006.01)
*A61P 25/28* (2006.01)
*A61P 35/00* (2006.01)

(52) U.S. Cl.
CPC ........... *C07D 213/65* (2013.01); *A61P 25/28* (2018.01); *A61P 35/00* (2018.01)

(58) Field of Classification Search
CPC ......... C07D 213/65; A61P 25/28; A61P 35/00
See application file for complete search history.

(56) References Cited

FOREIGN PATENT DOCUMENTS

| | | | |
|---|---|---|---|
| EP | 3 696 170 | A1 | 8/2020 |
| JP | 2017-500291 | A | 7/2016 |
| WO | WO2015-075082 | A1 | 11/2014 |
| WO | WO2017021319 | A1 * | 9/2017 |
| WO | WO2022/023315 | A1 * | 3/2022 |

OTHER PUBLICATIONS

Lazarevic-Pasti et al. (Current Medicinal Chemistry 2017, 24, 3283-3309) (Year: 2017).*
Calas et al: "Efficacy Assessment of an Uncharge REactivator of N0P-Inhibited Acetylcholinesterase Based on Tetrahydroacridine Pyridine-Aldoxime Hybrid in Mouse Compared to Pralidoxime", Biomolecules, vol. 10, No. 6, Jun. 4, 2020.
Kliachyna et al: "Design, synthesis and biological evaluation of novel tetrahydroacridine pyridine-aldoxime and -amidoxime hybrids as efficient uncharged reactivators of nerve agent-inhibited human acetylcholinesterase", European Journal of Medicinal Chemistry, vol. 78, p. 455-467, Mar. 15, 2014.
Lo et al: "In Silico Studies in Probing the Role of Kinetic and Structural Effects of Different Drugs for the Reactivation of Tabun-Inhibited AChE", PLOS One, vol. 8, No. 12, Dec. 2, 2013.
Mercey et al: "First efficient uncharged reactivators for the dephosphylation of poisoned human acetylcholinesterase", Chemical Communications, vol. 47, No. 18, p. 5295-5297, Mar. 31, 2011.
Renou et al: "Syntheses and in vitro evaluations of uncharged reactivators for human actylcholinesterase inhibited by organophosphorus nerve agents", Chemico-Biological Interactions, vol. 203, No. 1, p. 81-84, Mar. 1, 2013.
Renou et al: "Tryptoline-3-hydroxypyridinaldoxime conjugates as efficient reactivators of phosphylated human acetyl and butyrylcholinesterases", Chemical Communications, vol. 50, No. 30, p. 3947-3950, Apr. 1, 2014.
Zorba et al: "Pharmacokinetic Evaluation of Brain Penetrating Morpholine-3-hydroxy-2-pyridine Oxime as an Antidote for Nerve Agent Poisoning", Acs Chemical Neuroscience, vol. 11, No. 7, p. 1072-1084, Apr. 1, 2020.

(Continued)

*Primary Examiner* — Brandon J Fetterolf
(74) *Attorney, Agent, or Firm* — WCF IP

(57) ABSTRACT

The present invention relates to a compound of formula (I). It also relates to a pharmaceutical composition comprising at least one compound of formula (I) and at least one pharmaceutically acceptable support. Finally, it relates to the use of such a compound as a medicine, preferably in the treatment of a nervous and/or respiratory failure due to intoxication with at least one organophosphorous nerve agent; in the treatment of neurological diseases such as Alzheimer's disease; and/or in the treatment of cancer.

9 Claims, No Drawings

(56) References Cited

OTHER PUBLICATIONS

Katz et al, ChemBioChem. 2015, 16, 2205-2215.
De Koning et al, Eur. J. Med. Chem. 2018, 157,151-160.
Cadieux et al, Chemico-Biological Interactions 2016, 259, 133-141.
Guarna et al., J. Med. Chem., 2010, 53, 7119-7128.
Zueva I, Dias J, Lushchekina S, et al. New evidence for dual binding site inhibitors of acetylcholinesterase as improved drugs for treatment of Alzheimer's disease. Neuropharmacology. 2019;155:131-141. doi:10.1016/j.neuropharm.2019.05.025.
Zorbaz, Chem. Eur. J. (2018) 24:9675-9691.
Mercey, J. Med. Chem. (2012) 55:10791-10798.
Japanese Office Action 2023-516523 issued Jun. 24, 2025.

* cited by examiner

HYDROXY-PYRIDINALDOXIME SCAFFOLDS

The present invention relates to novel compounds having a hydroxy-pyridinaldoxime scaffold. Such compounds may be useful for many therapeutic and non-therapeutic applications. The invention also relates to compositions, notably pharmaceutical compositions, comprising said compounds, and their use.

Organophosphorous nerve agents (OPNA) are extremely toxic compounds that comprise chemical warfare agents (CWA) including sarin, soman, cyclosarin, tabun, methylphosphonothioate (VX) and pesticides such as paraoxon, parathion and tetraethyl pyrophosphate (TEPP). Their acute toxicity results from the irreversible inhibition of acetylcholinesterase (AChE) through phosphylation of its catalytic serine, which results in the inability of the enzyme to hydrolyze acetylcholine (ACh). Accumulation of this neurotransmitter at cholinergic synapses occurs, leading to a permanent saturation of the muscarinic and nicotinic receptors which ultimately results in seizure and respiratory arrest. Depending on the class of OPNA and on the administrated dose, death can occur within a few minutes.

Due to the similarity between the chemical precursors of CWA and pesticides, and to the relatively simple chemistry involved in their synthesis, efforts to control the proliferation of these agents have proved of limited success. Therefore, the development of effective measures to counteract OPNA poisoning remains a challenging issue to protect and treat both civilian and military populations. The current treatment for OPNA poisoning consists in the administration of a combination of atropine (antimuscarinic agent) and diazepam (anticonvulsant drug), to limit convulsions, and of a standard pyridinium oxime (pralidoxime, trimedoxime, HI-6, obidoxime, or HLö-7) to reactivate AChE. Oximes exert their action on OPNA-inhibited AChE by attacking the phosphorous atom of the phosphylated serine, leading to the removal of the phosphonate and restoration of the enzyme's catalytic activity. However, it has been demonstrated that the current therapy results in unequal efficiency, and none of these oximes offer broad efficacy across the different OPNAs. Further limitations of oxime-based therapy include inability to cross the blood-brain barrier (BBB), inability to reactivate the "aged" enzyme, and rapid clearance from the circulation when tested in vivo. Animal model studies and recent clinical trials using pesticide poisoned individuals have shown uneven clinical benefits of these oximes, and even harm, so their true efficacy as antidotes has been debated at the World Health Organisation.

To overcome the disadvantages of the current medication, the development of new broad spectrum and bioavailable centrally active drugs is of crucial importance.

Over the past decades, there has been a growing interest in the development of non-ionic oximes reactivators of OPNA-inhibited hAChE (human AChE) to increase BBB permeability. For example, uncharged hybrid reactivators bearing 3-hydroxy-2-pyridinaldoxime as nucleophilic moiety and a peripheral site AChE ligand, exhibited increased affinity for the phosphylated enzyme, a large spectrum of reactivation and the ability to cross efficiently the BBB in vitro.

Recently, unusual non-oxime non-ionic new functional groups such as Mannich phenols that are capable of reactivating OPNA-inhibited AChE have been reported by Katz, Cadieux and De Koning (Katz et al, *ChemBioChem.* 2015, 16, 2205-2215; de Koning et al, *Eur. J. Med. Chem.* 2018, 157, 151-160; Cadieux et al, *Chemico-Biological Interactions* 2016, 259, 133-141). However, the mechanism of the reactivation is still unclear, and the development of these molecules is hampered by their low stability in biological media.

Recent findings have demonstrated the ability of a zwitterionic, centrally acting, brain penetrating oxime to reverse severe symptoms and rapidly reactivate sarin- and paraoxon inhibited AChE in vivo.

It is further obvious that the above-mentioned compounds are accessed only after tedious, non-flexible and lengthy multistep chemical synthesis due to their increased structural complexity.

Despite these innovative strategies for the development of reactivators, efforts towards shorter and more convergent synthetic routes to innovative broad spectrum and centrally effective antidotes are still needed. There is thus a remaining need for chemical compounds efficient in therapeutic applications, particularly against OPNA intoxications, with a broad spectrum and centrally effective. These compounds have to be quick and easy to synthetize.

Surprisingly, the inventors have now discovered that specific compounds, having a specific hydroxy-pyridinaldoxime scaffold, fulfill these needs.

Indeed, such compounds are quick and very easy to produce thanks to a late-stage Sonogashira cross-coupling reaction of bromothiazoloximes isomers, which leads to a short and expedient synthesis, without using protecting groups for the sensitive oximes. The compounds present very interesting properties: they have a low molecular weight, and exhibit a quite simple molecular structural design and a broad spectrum of reactivation of OPNA-inhibited AChE, especially with increased efficacy for VX, sarin, tabunand paraoxon. These compounds exhibit a broad spectrum of reactivity.

Notably, these compounds may be used as antidotes against OPNA intoxications or as detoxifying or decontamination agents against organophosphorus compounds, or as sensors for OPNA detection, thanks to their effective and fast reactivation of hAChE without denaturing the same. They may also be used in the treatment of neurodegenerative diseases such as Alzheimer's disease. Finally, particularly the oxime compounds of the invention may be used as histone deacetylases (HDAC) inhibitors; consequently, they may be used in the treatment of cancer.

Thus, a first object of the present invention is a compound of formula (I):

(I)

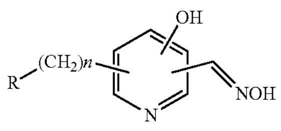

wherein the different groups are as defined in the detailed description below.

Another object of the present invention is a process for preparing the compounds of formula (I), especially by a Sonogashira reaction, as detailed below.

Another object of the present invention is a pharmaceutical composition comprising at least one compound of formula (I) and at least one pharmaceutically acceptable support.

Another object of the invention is a compound according to the invention, for use as a medicine.

A further object of the invention is a compound according to the invention for use in the treatment of a nervous and/or respiratory failure due to intoxication with at least one organophosphorous nerve agent.

Still a further object of this invention is a compound according to the invention for use in the treatment of neurological diseases such as Alzheimer's disease.

Still a further object of this invention is a compound according to the invention for use in the treatment of cancer.

A first object of the present invention is a compound of formula (I), or one of its pharmaceutically acceptable salts:

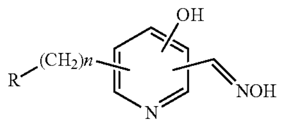

(I)

wherein:

- n is an integer from 2 to 4; and
- R is an alkyl group, a heteroalkyl, an aryl preferably not substituted, a heterocycloalkyl, a biomolecule, a carboxyl group, a hydroxyl group, a cyano, an oxime, an hydroxamic group, a ketone, a thiol or thioether or thioester group, a phosphate, a phosphonate, phosphinate, phosphonium, sulfone, sulfonium, sulfate group, a fluorescent probe, or a group —N(R1)(R2), wherein R1 and R2 are each independently H, an alkyl group or an aryl, or R1 and R2 form together a heterocycloalkyl group comprising at least two nitrogen atoms.

The compounds of the invention have a hydroxyl-pyridinaldoxime scaffold.

By "pharmaceutically acceptable salt", it is meant any salt of a compound of formula (I) with an acid or a base. Preferably, the pharmaceutically acceptable salt is a chlorhydrate salt (also called hydrochloride). Such a salt may be obtained by using HCl. More preferably, R comprises a nitrogen atom, which is complexed with HCl.

Preferably, the compound of the invention is a salt of a compound of formula (I), more preferably a chlorhydrate salt of a compound of formula (I).

The compound of formula (I) may be labeled with one or more isotopes such as $^{15}N$, $^{18}O$, $^{2}H$ or $^{3}H$. Preferably the compound is labeled on the =N—OH group, with $^{15}N$. Indeed, such a stable, non-toxic and non-radioactive isotope would allow in vivo and in vitro biological studies and profiling.

By "alkyl", it is meant a linear hydrocarbon group preferably comprising from 1 to 20 carbon atoms, in particular from 1 to 15 carbon atoms, or a branched or cyclic hydrocarbon group comprising from 3 to 20 carbon atoms. A cyclic hydrocarbon group is called a cycloalkyl group. Examples of alkyl groups include methyl, ethyl, n-propyl, isopropyl, n-butyl, isobutyl, tert-butyl, n-pentyl, isopentyl, n-hexyl, n-tridecyl, cyclohexyl and cyclohexylmethyl groups, and preferably ethyl, propyl, n-hexyl, n-tridecyl, cyclohexyl or cyclohexylmethyl group.

By "heteroalkyl", it is meant a heteroatom that is linked to any alkyl group. The heteroatom may be nitrogen, oxygen, sulfur, phosphorous or boron. A preferred heteroalkyl group is an alkoxy group. By "alkoxy", it is meant an oxygen linked to any alkyl group (—O-alkyl).

By "aryl", it is meant a monocyclic or polycyclic aromatic hydrocarbon group, which may be optionally substituted. Preferably, the aryl group is a phenyl, or a polycyclic aromatic hydrocarbon (PAH). A preferred PAH is pyrene. The aryl is preferably not substituted.

A "heterocycloalkyl" refers to a non-aromatic saturated monocyclic or polycyclic ring comprising carbon and hydrogen atoms, in which at least one carbon atom of the ring is substituted by a heteroatom. The heteroatom may be nitrogen, oxygen, or sulfur. Preferably, the heterocycloalkyl group is a monocyclic ring comprising from 3 to 6, preferably from 4 to 6 carbon atoms. Preferably, the heterocycloalkyl group is an epoxide, morpholino, pyrazolidine, oxathiolane, tetrahydrofuran, dioxolane, piperidine, piperazine, thiomorpholine, tetrahydropyrane, oxetane or azetidine. The heterocycloalkyl may be substituted or not.

The heterocycloalkyl group comprising at least two nitrogen atoms refers to a non-aromatic saturated monocyclic or polycyclic ring comprising carbon and hydrogen atoms, in which at least two carbon atoms of the ring are each substituted by a nitrogen atom.

Preferably, the heterocycloalkyl group is piperazine. Preferably one of the heteroatom, preferably nitrogen, is substituted by at least one protecting group, preferably tert-butyloxycarbonyl (Boc). Preferably the heterocycloalkyl group is 4-NBoc-piperazine. Alternatively, preferably, the heterocycloalkyl group is piperazine, and is not substituted.

By "biomolecule", it is meant a sugar moiety, a peptide moiety, an antibody, a virus, a DNA, a RNA or a protein moiety. The sugar moiety may be for example a glucose, fructose or sucrose moiety. A peptide moiety is a moiety typically comprising 1 to 50 amino acids. A protein moiety is a moiety typically comprising at least 51 amino acids, preferably from 60 to 500 amino acids.

By "carboxyl group", it is meant a —COOH group.

By "cyano", it is meant a —CN group.

By "oxime", it is meant a —C(R')=N—OH group, wherein R' is H, an alkyl group or an amine group —NR3R4, wherein R3 and R4 are each H or an alkyl group. When R' is —NR3R4, then the oxime is an amidoxime group.

By "hydroxamic group", it is meant a R5-C(O)—N(OH)— or —C(O)—N(OH)—R5 group, wherein R5 is H or an alkyl group.

By "ketone", it is meant a group comprising the moiety —CO—.

By "thiol, thioether or thioester group", it is respectively meant a group comprising a moiety —SR6, wherein R6 is respectively H, alkyl or —CO—R7, wherein R7 is an alkyl group.

By hydroxyl group, it is meant a group —OH.

By "phosphonate", it is meant a group $—P(O)(OR8)_2$, wherein R8 are identical or different and are either H or an alkyl group. When both R8 are H, then the group is a phosphate, i.e. a group $—P(O)(OH)_2$.

By "phosphinate", it is meant a group $—P(O)(OR_9)$, wherein R9 is H or an alkyl group.

By "phosphonium", it is meant a cation $P(R10)_4^+$, wherein each R10 (identical or different) is an alkyl group.

By "sulfone", it is meant a group comprising a radical —SO2.

By "sulfonium", it is meant a cation $S(R11)_3^+$, wherein each R11 (identical or different) is an alkyl group.

By "sulfate group", it is meant —SO4.

By "fluorescent probe", it is meant a chemical function or a fluorophore endowed with fluorescent properties. The fluorescent moiety may be for example a fluoresceine, boron dipyrromethene (BODIPY), a coumarine, a cyanine, an Alexa Fluor, an acridine, a fluorone, a squaraine, a phenanthridine, a cyanine, an oxazine, a perylene, an anthracene or rhodamine moiety.

Preferably, R is a group —N(R1)(R2), wherein R1 and R2 are each independently H, an alkyl group or an aryl, or R1 and R2 form together a heterocycloalkyl group comprising at least two nitrogen atoms.

Preferably, in formula (I), the hydroxy group (—OH) is in position 3.

Preferably, in formula (I), the oxime group is in position 2.

Preferably, in formula (I), the group —(CH2)n-R is in position 6.

Preferably, in formula (I), n is 3 or 4, preferably 4.

Preferably, in formula (I), R is a group —N(R1)(R2), wherein R1 and R2 are each independently H or R1 and R2 form together a heterocycloalkyl group comprising at least two nitrogen atoms, preferably a substituted piperazine or an unsubstituted piperazine.

Preferably, the compound of the invention is a 6-substituted-3-hydroxy-2-pyridinaldoxime of formula (II) or one of its pharmaceutically acceptable salts:

(II)

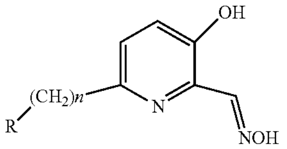

Preferably, n is 3 or 4, preferably 4.

Preferably, R is a group —N(R1)(R2), wherein R1 and R2 are each independently H or R1 and R2 form together a heterocycloalkyl group comprising at least two nitrogen atoms. Preferably, R is —NH2. Alternatively, preferably, R is a substituted piperazine, preferably 4-Boc-piperazine. Alternatively, preferably, R is an unsubstituted piperazine.

Preferably, the compound of formula (I) or (II) or one of its pharmaceutically acceptable salts is chosen from the following compounds:

(Z)-6-(4-aminobutyl)-3-hydroxypicolinaldehyde oxime JY-69:

JY-69

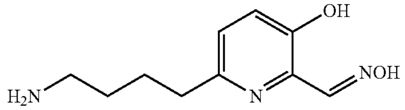

Tert-butyl (E)-4-(4-(5-hydroxy-6-((hydroxyimino)methyl) pyridin-2-yl)butyl)piperazine-1-carboxylate AMI 318:

AMI 318

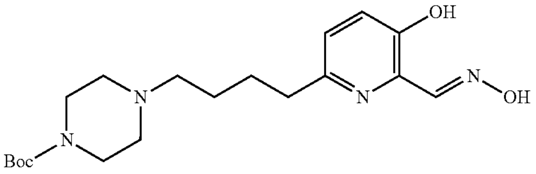

and 3-hydroxy-6-(4-(piperazin-1-yl)butyl)picolinaldehyde oxime RB6:

RB6

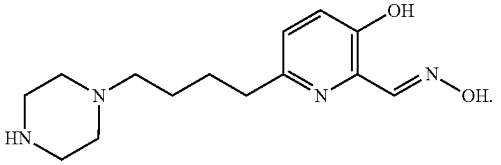

Preparation of the Compounds of Formula (I)

A compound of formula (I) according to the invention may be synthesized by any appropriate method as shown in the scheme below:

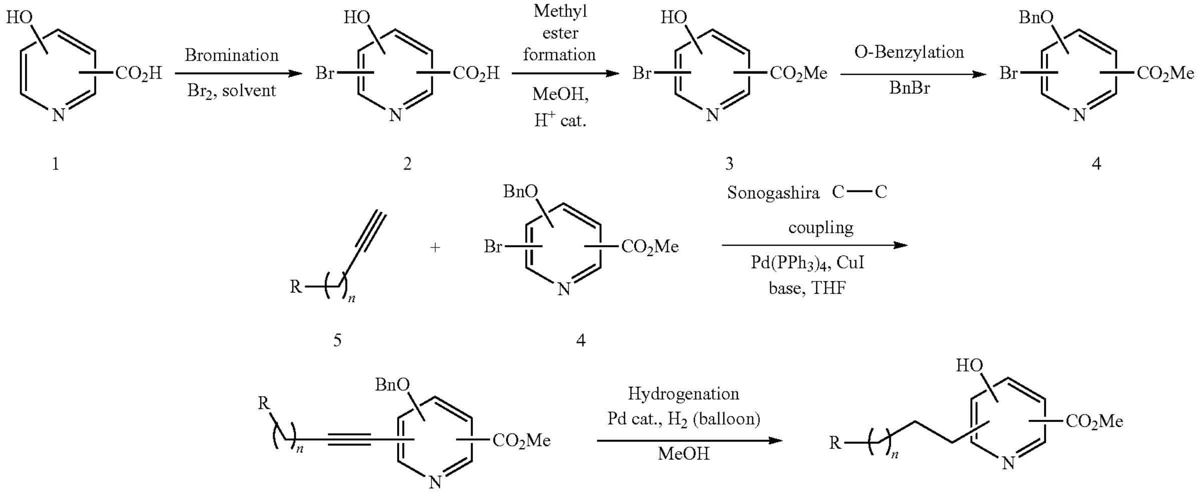

1 2 3 4

5 4

6 7

-continued

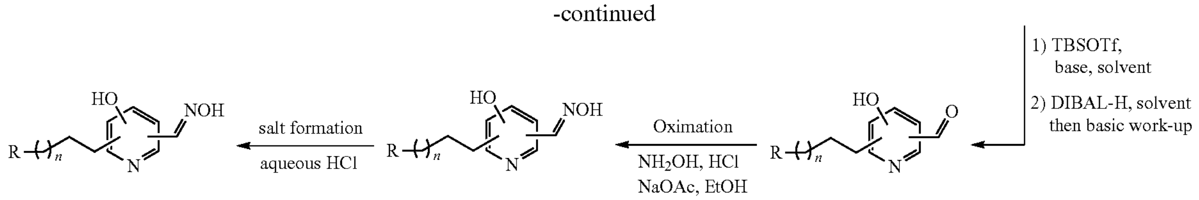

10 9 8

Such methods are exemplified in the following examples.

Preferably, the compounds of formula (I) are synthesized as described above. Such a process is chemoselective. Particularly, it does not necessitate any previous protection step of the oxime. Said process comprises a minimal number of steps (one or two), is quickly performed, at ambient temperature.

The main steps are as follows, as explained in the above scheme:

Hydroxypicolinic acid 1 is subjected to bromination using molecular bromine to afford bromo-hydroxypicolinic acid 2. Subsequent methyl ester formation (i.e. 3) followed by protection of the hydroxyl group with benzyl group upon treatment with benzyl bromide, afford protected methyl ester 4. 4 is then engaged in a Sonogashira C—C cross-coupling reaction with the appropriate functionalized terminal alkyne 5 to yield 6 as the coupled product. Hydrogenation of 6 affords the saturated deprotected hydroxypicolinic methyl ester 7. Temporary protection of the hydroxyl group using TBSOTf (tert-butyldimethylsilyl trifluoromethanesulfonate), followed by in situ controlled DiBAL-H (diisobutylaluminium hydride) methyl ester reduction provide the hydroxyl aldehyde 8, which upon treatment with hydroxylamine give oxime 9. 9 is then converted to the hydrochloride salt by treatment with aqueous HCl at room temperature.

Alternatively, an other halogenated compound, i.e. the iodine compound CV-66, is used (see preparation in the example section), instead of the bromo methyl ester compound 3.

Compounds 8 and 9 are compounds of formula (I) according to the invention.

Thus, the present invention also relates to a process for producing a compound of formula (I), comprising:

a Sonogashira C—C cross-coupling reaction of compound 4

4

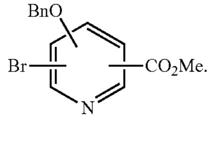

or of the corresponding iodine compound with the appropriate functionalized terminal alkyne 5

5

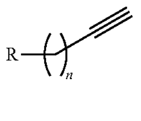

to yield the coupled product;

submitting said coupled product to a hydrogenation, to afford the corresponding saturated deprotected hydroxypicolinic methyl ester;

temporary protecting the hydroxyl group of the saturated deprotected hydroxypicolinic methyl ester, for example using TBSOTf, followed by a reduction step, for example in situ controlled DiBAL-H methyl ester reduction, to provide the hydroxyl aldehyde, treating the hydroxyl aldehyde with hydroxylamine to give the corresponding oxime of formula (I); and optionally, converting the oxime of formula (I) into its corresponding salt of formula (I), for example hydrochloride salt, for example by treatment with aqueous HCl.

Pharmaceutical Uses of the Compounds of the Invention

The compounds of this invention may be used in the treatment of a nervous and/or respiratory failure due to intoxication with at least one organophosphorous nerve agent which may preferably be selected from warfare agents such as O-ethyl S-[2-(diisopropylamino)ethyl] methylphosphonothioate (VX), tabun, sarin, cyclosarin and soman and pesticides such as paraoxon, parathion and tetraethyl pyrophosphate (TEPP). The compounds of the invention may be used in the treatment of a nervous and/or respiratory failure due to intoxication with at least one organophosphorous nerve agent, by virtue of their reactivation potency of organophosphorous inhibited cholinesterases, including acetylcholinesterase and butyrylcholinesterase. These compounds may alternatively be used in the treatment of diseases, which involve a reduced production of acetylcholine that may be overcome by the administration of acetylcholinesterase inhibitors. Examples of such diseases include in particular neurological diseases such as Alzheimer's disease.

These compounds may alternatively be used in the treatment of cancer, thanks to their action as inhibitors of histone deacetylases (HDAC).

The compound of this invention is usually included in a pharmaceutical composition comprising at least one compound according to the invention and a pharmaceutically acceptable support.

The amount of compound of formula (I) in the composition according to the invention may vary in a broad range depending upon the patient, the mode of administration and the expected effect.

The compound or composition according to the invention can be administered orally or non-orally, for instance via topical, parenteral, intramuscular, intravenous, cutaneous, nasal or rectal route.

The pharmaceutical composition of the invention can present different forms including granules, powders, tablets, capsules, syrups, emulsions, suspensions, and forms used for non-oral administration, for instance injections, sprays, transdermal patches or suppositories. These pharmaceutical forms can be prepared via known conventional techniques.

The preparation of an orally administered solid pharmaceutical form can be for instance performed by the following process: an excipient (for example lactose, sucrose, starch or mannitol), a desintegrant (for example calcium carbonate, calcium carboxymethylcellulose, alginic acid, sodium carboxymethylcellulose, colloidal silicon dioxide, sodium croscarmellose, crospovidone, guar gum, magnesium aluminium silicate, microcrystalline cellulose, cellulose powder, pregelatinised starch, sodium alginate or starch glycolate), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are added to the active principle and the mixture obtained is then tabletted. If necessary, the tablet can be coated via the known techniques, in order to mask the taste (for example with cocoa powder, mint, borneol or cinnamon powder) or to allow enteric dissolution or sustained release of the active principles. Coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide or quinoline yellow lake).

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, it is possible to add ethanol, propylene glycol or any other pharmaceutically acceptable non-aqueous solvent. The aqueous suspensions for oral use can be obtained by dispersing the finely divided active principle in water with a viscous product, such as a natural or synthetic gum or resin, methylcellulose or sodium carboxymethylcellulose.

The pharmaceutical forms for injection can be obtained, for example, by the following process. The active principle is dissolved, suspended or emulsified either in an aqueous medium (for example distilled water, physiological saline or Ringer's solution) or in an oily medium (for example olive oil, sesame seed oil, cottonseed oil, corn oil or propylene glycol), with a dispersant (for example Tween® 80, HCO® 60 (Nikko Chemicals), polyethylene glycol, carboxymethylcellulose or sodium alginate), a preserving agent (for example methyl p-hydroxybenzoate, propyl p-hydroxybenzoate, benzyl alcohol, chlorobutanol or phenol), an isotonicity agent (for example sodium chloride, glycerol, sorbitol or glucose) and optionally other additives, such as, if desired, a solubilizing agent (for example sodium salicylate or sodium acetate) or a stabilizer (for example human serum albumin).

Pharmaceutical forms for external use (topical use) can be obtained from a solid, semi-solid or liquid composition containing the active principle. For example, to obtain a solid form, the active principle can be treated with excipients (for example lactose, mannitol, starch, microcrystalline cellulose or sucrose) and a thickener (for example natural gums, cellulose derivatives or acrylic polymers) so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator (for example carbonic acid, phosphoric acid, citric acid, hydrochloric acid or sodium hydroxide) and a preserving agent (for example a p-hydroxybenzoic acid ester, chlorobutanol or benzalkonium chloride).

A method for the treatment of a nervous and/or respiratory failure due to intoxication with at least one organophosphorous nerve agent, comprising administering at least one compound according to the invention is also described herein.

A method for the treatment of a neurological disease such as Alzheimer's disease, comprising administering at least one compound according to the invention is also described herein.

A method for the treatment of a cancer, comprising administering at least one compound according to the invention is also described herein.

A method for the treatment of a virus, comprising administering at least one compound according to the invention is also described herein.

Within the context of the invention, the term treatment denotes curative, symptomatic, and/or preventive treatments. In particular, it can refer to reducing the progression of the disease, reducing or suppressing at least one of its symptoms or complications, or improving in any way the state of health of patients.

The administration of the compounds or of the composition according to the invention may be performed before, during or after the exposition of the subject to the organophosphorous nerve agent.

In the present invention, the terms "subject" and "patient" are used indifferently and designate a human subject.

The amount of compound according to the invention to be administered according to the invention may vary in a broad range depending upon the patient, the mode of administration and the expected effect. In particular, the amount of compound according to the invention may be comprised between 200 mg and 4000 mg, with up to 3 daily intakes.

The compound or composition according to the invention may be co-administered with at least one other active agent, such as an antimuscarinic agent, in particular atropine, an anticonvulsant, in particular diazepam or one of its prodrugs, such as avizafone, and/or a bioscavenger able to capture and/or degrade OPNAs in blood, such as human butyrylcholinesterase.

The term co-administered means that the administration of the compound or composition according to the invention and that of the other active agent can be simultaneous, sequential and/or separate.

Other Uses of the Compounds of the Invention

The compounds of this invention may further be used as tools for in vivo and/or in vitro biological studies. In this application, the compounds according to the invention may include one or more isotopes, which will allow for their detection.

The following examples are provided as illustrative, and not limitative, of the present invention.

EXAMPLES

Example 1: Synthesis of Compounds of the Invention

General Methods

All starting materials and reagents were purchased from commercial sources, and used as received without further purification. Air and $H_2O$ sensitive reactions were performed in flame dried glassware under Ar atmosphere. Moisture sensitive reagents were introduced via a dry syringe. Anhydrous solvents were supplied over molecular sieves, and used as received. Petroleum ether (PE) refers to the 40-60° C. boiling fraction. Reactions were monitored by thin-layer chromatography (TLC) with silica gel 60 $F_{254}$ 0.25 mm pre-coated glass plates. Compounds were visualized by using $UV_{254}$ and/or phosphomolybdic acid stain [3 g $12MoO_3 \cdot H_3PO_4 \cdot xH_2O$ in 100 mL EtOH] followed by heating with a heat gun. Flash column chromatography was performed using Macherey-Nagel silica gel 60 (15-40 μm). NMR experiments were recorded with a Bruker Avance 400 spectrometer at 400 MHz for $^1H$ nuclei and at 100 MHz for $^{13}C$ nuclei. The chemical shifts are expressed in part per million (ppm) relative to TMS (δ=0 ppm) and the coupling constant J in Hertz (Hz). NMR multiplicities are reported using the following abbreviations: br=broad, s=singlet, d=doublet, t=triplet, q=quadruplet, m=multiplet. HRMS were recorded on a Bruker micrOTOF spectrometer.

EXPERIMENTAL PROCEDURES

Synthesis of JY69

Scheme 1

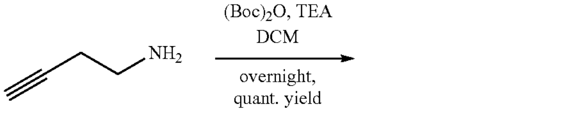

21

22

Scheme 2

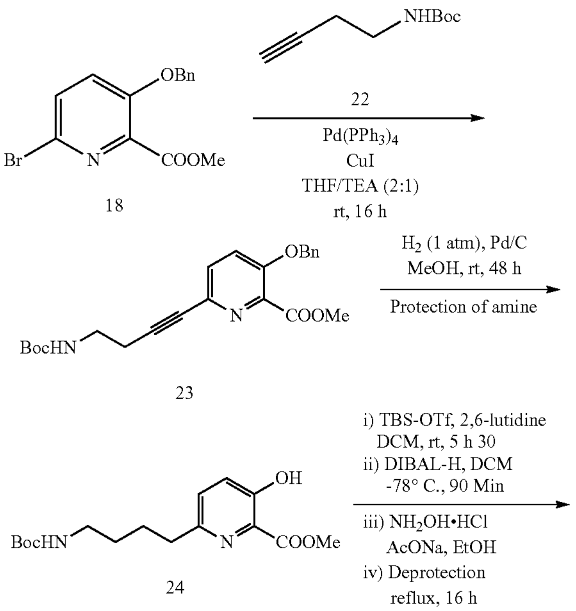

22

18

23

24

-continued

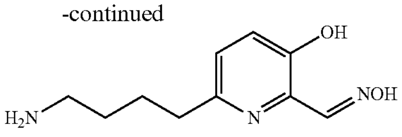

14 (JY 69)

tert-Butyl but-3-yn-1-ylcarbamate 22

22

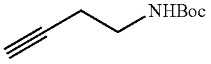

To a solution of 1-amino-3-butyne 21 (240 μL/200 mg, 2.894 mmol, 1 equiv), in dry THF (10 mL) were added triethylamine (8070 μL, 5.788 mmo, 2 equivl) and $(Boc)_2O$ (695 mg, 3.18 mmol, 1.1 equiv). Then the resulting mixture was stirred for overnight at room temperature. After completion, the reaction mixture was concentrated under reduced pressure and the residue was purified by column chromatography (EtOAc/Cy Hex 1:9) to afford the desired Boc compound 22 as an oil (quantitative yield). The spectroscopic and analytical data of synthetic compound 22 were in excellent agreement with the reported values.

Methyl 3-(benzyloxy)-6-(4-((tert-butoxycarbonyl) amino)but-1-yn-1-yl)picolinate 23

23

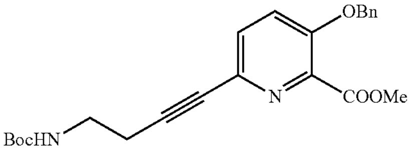

To a degassed solution of methyl 3-benzyloxy-6-bromopicolinate 18 (835 mg, 2.60 mmol, 1.1 equiv) in THF/Et 3 N (15 mL/10 mL), $Pd[PPh_3]_4$ (274 mg, 0.237 mmol, 0.1 equiv) and CuI (90 mg, 0.474 mmol, 0.2 equiv) were added. After degassing the reaction mixture for 5 min at room temperature, a degassed solution of the previous carbamate 22 (400 mg, 2.37 mmol, 1 equiv) in THF (10 mL) was added dropwise and the reaction mixture was stirred at the room temperature (rt) for 16 h. After completion, the reaction mixture was concentrated under reduced pressure and the residue was purified by column chromatography ($CH_2Cl_2$/MeOH 9:1) to afford the desired picolinate 23 as thick syrup (900 mg, 98%). IR (neat) $v_{max}$ 2976, 1731, 1696, 1500, 1450, 1267, 1207, 1165, 1097, 831, 736, 695 $cm^{-1}$; $^1H$ NMR (400 MHz, $CDCl_3$) δ (ppm) 7.24-7.46 (m, 7H, Ar), 5.20 (s, 2H, $-CH_2Bn$), 4.97 (br s, 3H, Me), 3.35 (q, =6.4, 12.5 Hz, 2H, $H_{10}$), 2.59 (t, J=6.4 Hz, 2H, $H_9$), 1.44 (s, 9H, Boc); $^{13}C$ NMR (100 MHz, $CDCl_3$) δ (ppm) 164.61, 155.60, 153.02, 139.74, 135.30, 134.85, 130.12, 128.58, 128.09, 126.76, 121.69 (Ar), 87.56 (C8), 80.31 (C7), 79.26 (–Boc), 70.67 (—$CH_2Ph$), 52.58 (Me), 39.00 (C10), 28.24 (–Boc), 20.83 (C9); HRMS ($ESI^+$) m/z calcd for $C_{23}N_{27}N_2O_5^+$ 411.1871 found 411.1914.

Methyl 6-(4-((tert-butoxycarbonyl)amino)butyl)-3-hydroxypicolinate 24

24

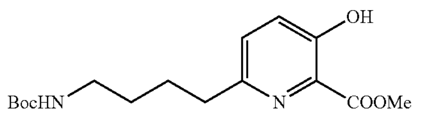

To a degassed solution of picolinate 23 (850 mg, 2.195 mmol, 1 equiv) in dry MeOH (6+0 mL), Pearlman's catalyst $Pd(OH)_2/C$ (20% with 50% moisture, 93 mg, 0.658 mmol, 0.3 equiv) was added. After evaporating and flushing with $H_2$ three times, the reaction mixture was stirred at room temperature under $H_2$ (1 atm.) for 16 h. Upon completion, the catalyst was removed by filtration through a short column of celite, the solvent was evaporated, and the residue 24 (550 mg) was directly subjected for the following step without purification. IR (neat) $v_{max}$ 3357, 2925, 1683, 1536, 1457, 1365, 1277, 1169, 1098, 739, 670, 590 $cm^{-1}$; $^1H$ NMR (400 MHz, $CDCl_3$) δ (ppm) 10.57 (s, 1H, OH), 7.27 (s, 2H, Ar), 4.56 (s, 1H, —NH), 4.02 (s, 1H, -Me), 3.12 (q, =6.5, 2H, $H_{10}$), 2.80 (t, J=7.6 Hz, 2H, $H_7$), 1.71 (m, 2H, $H_8$), 1.52 (m, 2H, $H_9$), 1.41 (s, 9H, Boc); $^{13}C$ NMR (100 MHz, $CDCl_3$) δ (ppm) 170.09 (—COOMe), 157.21 (-Boc), 155.96 (C3), 153.58 (C6), 129.21 (C5), 128.78 (C2), 126.67 (C4), 79.07 (-Boc), 53.14 (-Me), 40.29 (C10), 37.04 (C7), 29.65 (C8), 28.40 (-Boc), 27.01 (C9); HRMS ($ESI^+$) m/z calcd for $C_{18}H_{25}N_2O_5^+$ 325.1800 found 325.1758.

(Z)-6-(4-aminobutyl)-3-hydroxypicolinaldehyde oxime 14 (JY-69)

14

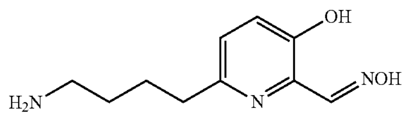

14. HCl

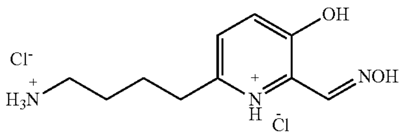

To a solution of deprotected picolinate 24 (100 mg, 0.309 mmol, 1 equiv) in dry $CH_2Cl_2$ (5 mL), 2,6-lutidine (99 μL, 0.927 mmol, 3 equiv), and tert-butyldimethylsilyltrifluoromethanesulfonate (141 μL, 0.617 mmol, 2 equiv) were successively added and the reaction mixture was stirred at the room temperature under argon atmosphere during 5 h. After completion, the reaction mixture was directly concentrated under reduced pressure to give silylated compound. After drying in vacuo, the residue was directly subjected to the following step.

To the solution of silylated compound (0.309 mmol, 1 equiv) in dry $CH_2Cl_2$ (5 mL) at −78° C., DIBAL-H (1M solution in $CH_2Cl_2$, 1.24 mL, 1.236 mmol, 4 equiv) was added dropwise. The reaction mixture was stirred at −78° C. for 90 min, then the reaction was quenched with MeOH (2 mL), and the cooling bath was removed. When the mixture was warmed to room temperature the solvent in reaction mixture was evoporated under reduced pressure to give aldehyde compound as crude along with aluminium salts. The salts were filtered by washing with $CH_2Cl_2$ (50 mL). The filtrate was evaporated, and the residue was directly subjected for the next step without purification.

A solution of picolinaldehyde (0.309 mmol, 1 equiv), hydroxylamine hydrochloride (43 mg, mmol, 2 equiv), and $CH_3CO_2Na$ (76 mg, 0.927 mmol, 3 equiv) in dry ethanol (6 mL) was stirred at reflux during 16 h. After concentration under reduced pressure, the crude product was washed with $CH_2Cl_2$ (5*10 mL) to remove all the impurities carrying from the last two reactions. The existing compound in the round bottom flask was picolinaldehyde oxime 6, which was dried in high vacuo (95 mg, 84%) and confirmed by 1H NMR. $^1H$ NMR (400 MHz, $CDCl_3$) δ (ppm) 8.20 (s, 1H, $H_{11}$), 7.29 (d, J=8.2 Hz, 1H, $H_5$), 7.19 (d, J=8.2 Hz, 1H, $H_4$), 2.95 (t, J=6.6, 2H, $H_{10}$), 2.77 (t, J=6.4, 2H, $H_7$), 1.90 (m, 9H, —Ac), 1.81-1.64 (m, 4H, $H_8$, $H_9$); $^{13}C$ NMR (100 MHz, $CDCl_3$) δ (ppm) 180.78, 180.75, 180.71 (-Ac), 153.99 (C3), 153.90 (C6), 152.53 (C12), 136.58 (C2), 126.37 (C5), 125.64 (C4), 40.53 (C10), 37.04 (C7), 28.19 (C8), 27.95 (C9), 24.39 (-Ac); HRMS ($ESI^+$) m/z calcd for $C_{10}H_{16}N_3O_2^+$210.

6. HCl Salt:

$^1H$ NMR (400 MHz, $CDCl_3$) δ (ppm) 8.46 (s, 1H, $H_{11}$), 7.94 (d, J=9.0 Hz, 1H, $H_4$), 7.71 (d, J=9.0 Hz, 1H, $H_5$), 3.02 (q, J=8.0, 2H, $H_1$, $H_{10}$), 1.86-1.69 (m, 4H, $H_8$, $H_9$); $^{13}C$ NMR (100 MHz, $CDCl_3$) δ (ppm) 153.45 (C3), 149.98 (C6), 142.46 (C11), 134.30 (C4), 131.15 (C2), 128.21 (C5), 39.66 (C10), 37.27 (C7), 26.71 (C8), 26.28 (C9).

Alternatively, the iodine compound CV-66 is used instead of bromo compound 18. It may be coupled to the alkyne via a Sonogashira coupling reaction as described above. It may be prepared as follows:

Synthesis of methyl 3-hydroxy-6-iodopicolinate CV-66

CV-66

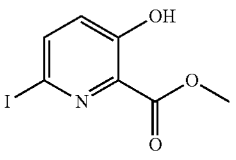

To a degassed solution of methyl-3-hydroxypicolinate (50 mg, 0.327 mmol, 1 eq) in dichloromethane (6 mL) was added N-iodosuccinimide (110 mg, 0.491 mmol, 1.5 eq) and the reaction mixture was stirred at room temperature for 72 h. After completion (monitored by TLC), 10 mL of dichloromethane were added and the mixture was transferred into a separating funnel. The organic layer was washed with a satured solution of $Na_2S_2O_3$ (15 mL) followed by brine (15 mL). The organic layer was dried over $Na_2SO_4$, concentrated in vacuo and purified by column chromatography (EtOAc/PE, 20%) to afford the desired methyl 3-hydroxy-6-iodopicolinate CV-66 as a white solid (20 mg, 22%), $R_f$ (20% EA+PE) 0.58; $^1H$ NMR (400 MHz, $CDCl_3$) δ 10.67 (s, 1H), 7.76 (d, J=8.7 Hz, 1H), 7.06 (d, J=8.7 Hz, 1H), 4.04 (s, 3H). $^{13}C$ NMR (126 MHz, $CDCl_3$) δ 169.21, 159.16, 140.87, 131.62, 128.67, 104.41, 53.53.).

Synthesis of AMI 318:

The tosylate 2 has been prepared according to *Angew. Chem. Int. Ed.* 2009, 48, 2569-2571 from commercially available TsCl and 1-butyn-4-ol 1.

Scheme 3: Synthesis of tosylate 2

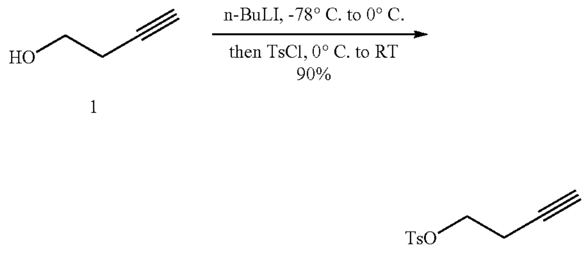

1

2

The chemoselective mono N-tert-butyloxycarbonylation of commercially available piperazine 3 to afford 4 has been performed as described in *Tetrahedron Letters* 53 (2012) 5803-5806. The tosylate 5 has been synthesized as described earlier in *Tetrahedron* 67 (2011) 9765e9770.

Scheme 4: Synthesis of Boc protected homopropargyl piperazine 6

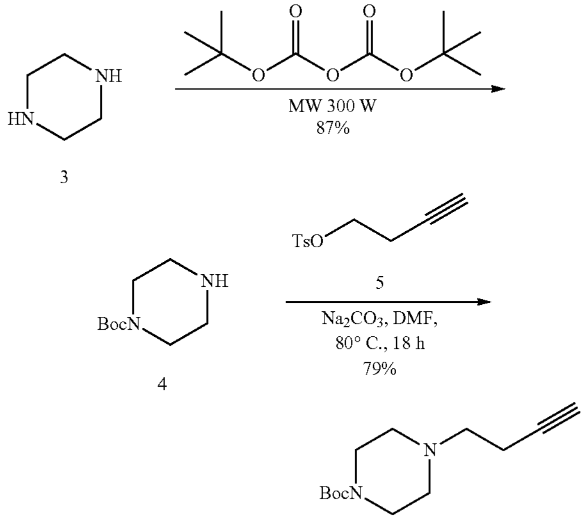

3

4

6

Scheme 5: Five step synthetic route from Boc protected homopropargyl piperazine 6 to final Boc-piperazine hybrid reactivator 9:AMI 318.

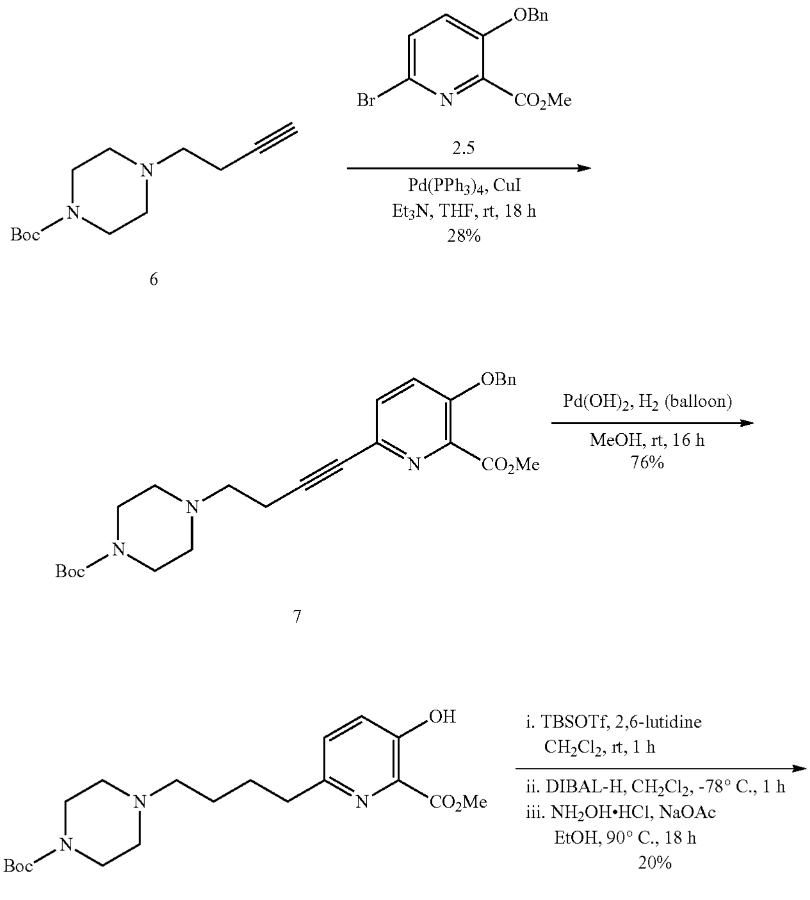

6

7

8

-continued

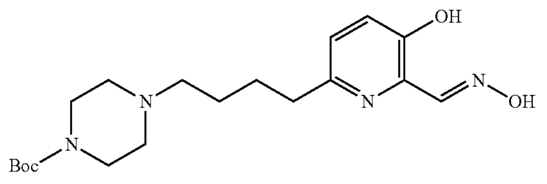

9:AMI 318

Tert-butyl 4-(but-3-yn-1-yl)piperazine-1-carboxylate (6)

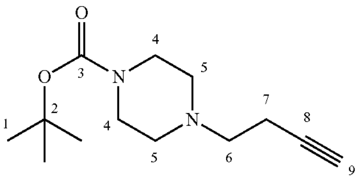 [SMILES: C#CCCN1CCN(C(=O)OC(C)(C)C)CC1]

Molecular weight: 238.2 g/mol, formula: $C_{13}H_{22}N_2O_2$

Following a procedure adapted from Guarna et al. (Guarna et al., *J. Med. Chem.,* 2010, 53, 7119-7128) for the substitution of piperazine, to a solution of 1-Boc-piperazine (2.00 g, 10.7 mmol, 1 equiv.) in EtOH (25 mL) was added DIPEA (5.32 mL, 32.2 mmol, 3 equiv.) and but-3-yn-1-yl p-toluenesulfonate (2.65 g, 11.8 mmol, 1.1 equiv.). The colourless reaction solution was stirred at 60° C. for 18 h. The volatiles were removed in vacuo and $CH_2Cl_2$ (15 mL) was added. The organic phase was washed (sat. aq. $Na_2CO_3$, 20 mL), dried ($MgSO_4$), filtered and concentrated in vacuo. The crude brown residue was purified by column chromatography ($SiO_2$, 10% MeOH in $CH_2Cl_2$) to afford benzyl 4-(but-3-yn-1-yl)piperazine-1-carboxylate (2.03 g, 8.51 mmol, 79%) as a yellow oil.

TLC $R_f$ 0.67 (10% MeOH in $CH_2Cl_2$, $SiO_2$)

$^1$HNMR (400 MHz, $CDCl_3$) δ 3.44 (t, J=5.1 Hz, 4H, $BocN(CH_2)_2$), 2.60 (t, J=7.4 Hz, 2H, $NCH_2CH_2CCH$), 2.48-2.32 (m, 6H, $(CH_2)_2NCH_2CH_2CCH$), 1.99 (t, J=2.7 Hz, 1H, $NCH_2CH_2CCH$), 1.46 (s, 9H, $C(CH_3)_3$) ppm $^{13}$CNMR (101 MHz, $CDCl_3$) δ 154.7 (3), 82.5 (8), 79.7 (2), 77.2 (9), 69.1 (6), 57.0 (5), 52.7 (4), 28.4 (1), 16.8 (7) ppm IR (neat) $v_{max}$ 3299 (b), 2975 (m), 2813 (s), 2119 (s), 1688 (s), 1166 (s) $cm^{-1}$ LRMS ($ESI^+$) m/z 239.3 $[M+H]^+$ HRMS ($ESI^+$) m/z calcd. for $C_{13}H_{23}N_2O_2$, 239.1754 m/z meas. 239.1755 $[M+H]^+$ Tert-butyl 4-(4-(5-(benzyloxy)-6-(methoxycarbonyl) pyridin-2-yl)but-3-yn-1-yl)piperazine-1-carboxylate (7)

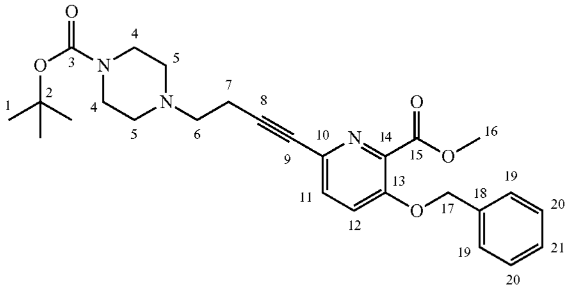 [SMILES: COC(=O)c1nc(C#CCCN2CCN(C(=O)OC(C)(C)C)CC2)ccc1OCc1ccccc1]

Molecular weight: 479.2 g/mol, formula: $C_{27}H_{33}N_3O_5$

To a degassed solution of benzyl 4-(but-3-yn-1-yl)piperazine-1-carboxylate (1.00 g, 4.20 mmol, 1 equiv.) in THF/Et 3 N (7 mL/3 mL) was added $Pd(PPh_3)_4$ (485 mg, 0.42 mmol, mol %) and CuI (160 mg, 0.84 mmol, 20 mol %). To the resulting orange reaction mixture was added dropwise a degassed solution of methyl 3-(benzyloxy)-6-bromopyridine-2-carboxylate (1.49 g, 4.62 mmol, 1.1 equiv.) in THF (10 mL). The brown solution was stirred for 18 h at rt. The reaction was concentrated in vacuo. The residue was purified by column chromatography ($SiO_2$, 50% EtOAc in hexanes to EtOAc) to afford tert-butyl 4-(4-(5-(benzyloxy)-6-(methoxycarbonyl)pyridin-2-yl)but-3-yn-1-yl)piperazine-1-carboxylate (564 mg, 1.18 mmol, 28%) as an orange oil.

TLC $R_f$ 0.32 (EtOAc, $SiO_2$)

$^1$HNMR (400 MHz, $CDCl_3$) δ 7.68-7.29 (m, 7H, ArH), 5.19 (s, 2H, $PhCH_2$), 3.94 (s, 3H, $CO_2CH_3$), 3.42 (t, J=7.9 Hz, 2H, $NCH_2CH_2CC$), 2.71-2.38 (m, 6H, BocN $(CH_2)_2$, $NCH_2CH_2CC$), 2.05 (br. s, 4H, $(CH_2)_2NCH_2CC$), 1.39 (s, 9H, $C(CH_3)_3$) ppm $^{13}$CNMR (101 MHz, $CDCl_3$) δ 170.1 (15), 153.0 (3), 135.5 (13), 132.2 (18), 132.0 (14), 131.9 (10), 129.9 (19), 128.8 (11), 128.6 (21), 128.4 (20), 128.3 (12), 126.9 (2), 121.8 (9), 88.2 (8), 80.1 (17), 70.9 (6), 60.4 (5), 56.8 (16), 52.7 (4), 52.6 (7), 28.4 (1) ppm IR (neat) $v_{max}$ 2974 (m), 2814 (m), 2232 (s), 1687 (s), 741 (s) $cm^{-1}$ LRMS ($ESI^+$) m/z 480.4 $[M+H]^+$ HRMS ($ESI^+$) m/z calcd. for $C_{27}H_{34}N_3O_5$, 480.2493 m/z meas. 480.2493 $[M+H]^+$ Tert-butyl 4-(4-(5-hydroxy-6-(methoxycarbonyl) pyridin-2-yl)butyl)piperazine-1-carboxylate (8)

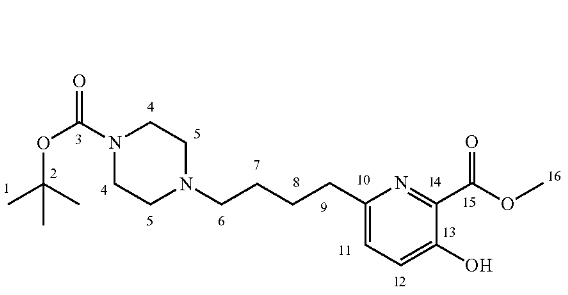 [SMILES: COC(=O)c1nc(CCCCN2CCN(C(=O)OC(C)(C)C)CC2)ccc1O]

Molecular weight: 393.2 g/mol, formula: $C_{20}H_{31}N_3O_5$

To a degassed suspension of tert-butyl 4-(4-(5-(benzyloxy)-6-(methoxycarbonyl)pyridin-2-yl)but-3-yn-1-yl)piperazine-1-carboxylate (500 mg, 1.04 mmol, 1 equiv.) in anhydrous MeOH (20 mL), was added Pearlman's catalyst (146 mg, 1.04 mmol, 1 equiv.). The reaction vessel was evacuated and flushed with hydrogen gas five times. The black reaction mixture was stirred for 18 h at rt. The catalyst was removed by filtration through Celite and the solvent was removed in vacuo. The residue was purified by column chromatography ($SiO_2$, EtOAc) to afford tert-butyl 4-(4-(5-hydroxy-6-(methoxycarbonyl)pyridin-2-yl)butyl)piperazine-1-carboxylate (310 mg, 0.79 mmol, 76%) as a yellow oil.

TLC $R_f$ 0.08 (EtOAc, $SiO_2$)

$^1$HNMR (400 MHz, $CDCl_3$) δ 10.61 (s, 1H, OH), 7.35-7.29 (m, 2H, ArH), 4.06 (s, 3H, $CO_2CH_3$), 3.44 (t, J=5.1 Hz, 4H, $BocN(CH_2)_2$), 2.83 (t, J=7.6 Hz, 2H, $NCH_2CH_2CH_2CH_2$), 2.41-2.34 (m, 6H, $(CH_2)_2NCH_2CC$, $NCH_2CH_2CH_2CH_2$), 1.80-1.68 (m, 2H, $NCH_2CH_2CH_2CH_2$), 1.63-1.51 (m, 2H, $NCH_2CH_2CH_2CH_2$), 1.48 (s, 9H, $C(CH_3)_3$) ppm $^{13}$CNMR (101 MHz, $CDCl_3$) δ 170.2 (15), 157.2 (3), 154.8 (13), 153.8 (14), 129.1 (11), 128.8 (10), 126.7 (12), 79.6 (2), 58.5 (4), 53.2 (5), 53.1 (16), 37.5 (6), 30.9 (7), 28.4 (9), 27.9 (8), 26.4 (1) ppm IR (neat) $v_{max}$ 3161 (m), 2932 (m), 2808 (m), 1689 (s), 1166 (s) $cm^{-1}$ LRMS ($ESI^+$) m/z 394.4 $[M+H]^+$ HRMS ($ESI^+$) m/z calcd. for $C_{20}H_{32}N_3O_5$, 394.2336 m/z meas. 394.2340 $[M+H]^+$ Tert-butyl (E)-4-(4-(5-hydroxy-6-((hydroxyimino) methyl)pyridin-2-yl)butyl)piperazine-1-carboxylate (9) (AMI 318)

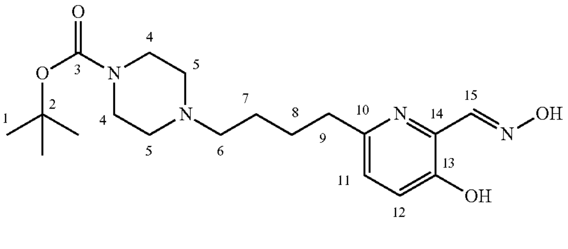 [SMILES: CC(C)(C)OC(=O)N1CCN(CCCCc2ccc(O)c(/C=N/O)n2)CC1]

Molecular weight: 378.2 g/mol, formula: $C_{19}H_{30}N_4O_4$

Following a procedure adapted from de Sousa (Thesis Julien De Sousa, University of Strasbourg: https://www.theses.fr/191793272), to a solution of tert-butyl 4-(4-(5-hydroxy-6-(methoxycarbonyl)pyridin-2-yl)butyl)piperazine-1-carboxylate (200 mg, 0.51 mmol, 1 equiv.) in anhydrous $CH_2Cl_2$ (5 mL), was added 2,6-lutidine (0.18 mL, 1.52 mmol, 3 equiv.) and TBSOTf (0.23 mL, 1.02 mmol, 2 equiv.), and the yellow solution was stirred at rt, under an Ar atmosphere for 5 h. The solvent was removed in vacuo, and the crude ester was taken up in anhydrous $CH_2Cl_2$ (5 mL), then cooled to −78° C. DIBAL-H (1.0 M in $CH_2Cl_2$, 1.53 mL, 1.52 mmol, 3 equiv.) was added dropwise and the reaction was stirred at −78° C. for 1 h. MeOH (5 mL) was added and the reaction mixture was allowed to warm to rt. The solvent was removed in vacuo, $CH_2Cl_2$ (35 mL) was added, and the white aluminium salts were removed by filtration. The filtrate was concentrated in vacuo and anhydrous EtOH (10 mL), $NH_2OH·HCl$ (71 mg, 1.02 mmol, 2 equiv.) and NaOAc (83 mg, 1.02 mmol, 2 equiv.) were added. The yellow reaction solution was heated to reflux for 18 h and upon cooling to rt, the solvent was removed in vacuo to afford tert-butyl (E)-4-(4-(5-hydroxy-6-((hydroxyimino)methyl)pyridin-2-yl)butyl)piperazine-1-carboxylate (38 mg, 0.10 mmol, 20%) as an orange solid.

Tert-butyl (E)-4-(4-(5-hydroxy-6-((hydroxyimino) methyl)pyridin-2-yl)butyl)piperazine-1-carboxylate (10 mg, 0.03 mmol) was dissolved in 2 M HCl (3 mL). The orange solution was stirred at rt for 10 mins. The reaction solution was concentrated in vacuo to afford tert-butyl (E)-4-(4-(5-hydroxy-6-((hydroxyimino)methyl)pyridin-2-yl)butyl)piperazine-1-carboxylate hydrochloride (12.4 mg, 0.03 mmol, 100%) as a pale orange solid.

TLC $R_f$ 0.15 (EtOAc, $SiO_2$)

$^1$HNMR (400 MHz, MeOD-$d_4$) δ 8.30 (s, 1H, CHNOH), 7.30 (d, J=8.5 Hz, 1H, NCCHCH), 7.19 (d, J=8.5 Hz, 1H, NCCHCH), 3.33 (d, J=3.3 Hz, 4H, $BocN(CH_2)_2$), 2.77 (t, J=7.5 Hz, 2H, $NCH_2CH_2CH_2CH_2$), 2.56-2.43 (m, 6H, $(CH_2)_2NCH_2CC$, $NCH_2CH_2CH_2CH_2$), 1.79-1.68 (m, 2H, $NCH_2CH_2CH_2CH_2$), 1.65-1.53 (m, 2H, $NCH_2CH_2CH_2CH_2$), 1.47 (s, 9H, $C(CH_3)_3$) ppm $^{13}$CNMR (101 MHz, MeOD-$d_4$) δ 154.9 (3), 153.0 (13), 152.4 (14), 151.4 (15), 134.9 (10), 124.6 (11), 124.0 (12), 80.0 (2), 57.8 (6), 52.4 (5), 52.2 (4), 36.1 (9), 27.5 (7), 27.2 (1), 25.3 (8) ppm IR (neat) $v_{max}$ 3490 (b), 2974 (m), 2951 (m), 2863 (m), 1700 (s), 1166 (s) $cm^{-1}$ LRMS ($ESI^+$) m/z 379.4 $[M+H]^+$ HRMS ($ESI^+$) m/z calcd. for $C_{19}H_{31}N_4O_4$, 379.2340 m/z meas. 379.2341 $[M+H]^+$ MPt 130-131° C.

Synthesis of 3-hydroxy-6-(4-(piperazin-1-yl)butyl) picolinaldehyde oxime (RB6)

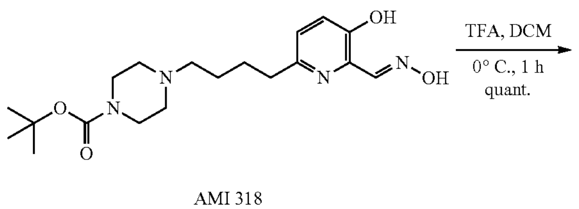

AMI 318

-continued

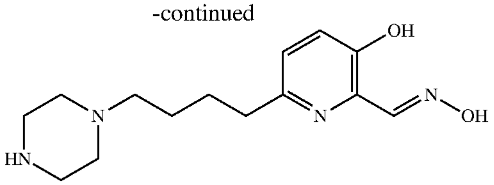

RB6

Tert-butyl-4-(4-(5-hydroxy-6-((hydroxyimino)methyl) pyridin-2-yl)butyl)piperazine-1-carboxylate (AMI 318) (25 mg, 0.07 mmol) was dissolved in 2.5 mL anhydrous dichloromethane (DCM), in a one neck round bottom flask kept under an Ar atmosphere at room temperature. The reaction was then kept at 0° C. A solution of trifluoroacetic acid (HPLC grade from Sigma-Aldrich) (100 μL) in 1 mL anhydrous DCM was added dropwise in the flask. The slightly yellow solution was stirred at 0° C. for 1 h. The reaction solution was concentrated in vacuo to afford 3-hydroxy-6-(4-(piperazin-1-yl)butyl)picolinaldehyde oxime RB6 in quantitative yield.

$^1$H NMR (400 MHz, $CD_3OD$) δ 8.28 (s, 1H), 7.28 (d, J=8.8 Hz, 1H), 7.16 (d, J=8.8 Hz, 1H), 3.78 (m, 4H), 2.77 (m, 2H), 2.67 (m, 4H), 2.49 (m, 2H), 1.73 (m, 2H), 1.55 (m, 2H).

LC/MS: Eluent gradient: water (+0.05% TFA)/acetonitrile (+0.1% TFA), 98:2 to 0:100.

Detection: UV (220 nm); Mass detection: ESI+ or ESI−

Exact mass: 278.17, Main Mass Peak found: 279.09 [M+1].

Example 2: In Vitro Reactivation of Human Acetylcholinesterase (hAChE) by Compounds of the Invention Compounds JY-69 and AMI 318 of the invention were tested for their reactivation properties of hAChE inhibited by O-ethyl S-[2-(diisopropylamino)ethyl] methylphosphonothioate (VX), tabun, sarin or paraoxon. 2-PAM (pralidoxime or 2-[(E)-(hydroxyimino)methyl]-1-methylpyridinium) and HI6 (asoxime chloride or [1-[(4-carbamoylpyridin-1-ium-1-yl)methoxymethyl]pyridin-2-ylidene]methyl-oxoazanium dichloride) were used as comparative compounds.

Inhibition of hAChE by OPNAs. Recombinant hAChE was produced and purified as previously described (see reference https://www.ncbi.nlm.nih.gov/pubmed/31132435). VX, sarin and tabun have been supplied by DGA maitrise NRBC (Vert le Petit, France).

Stock solutions of OPNA at 5 mM in isopropanol were used to inhibit the purified hAChE as previously described [Carletti, E. et al. 2008]. Briefly, a ten-fold excess of OPNA was used to perform the inhibition of hAChE in a sodium phosphate buffer (100 mM, pH 7.4, 0.1% BSA) at 25° C. Complete inhibition of hAChE was monitored by measuring the residual activity with a modified Ellman assay as previously described [Ellman, G. L., et al. 1961] and excess of OPNA were removed by using a desalting PD-10 column (GE Healthcare).

$IC_{50}$ measurements. Compounds were dissolved in water to make 40 mM stock solutions. Recombinant hAChE activity was measured spectrophotometrically at 25° C., monitoring the absorbance at 412 nm, in 1 mL of Ellman's buffer (0.5 mM DTNB, 0.1% BSA, 0.1 M phosphate, pH 7.4), in the presence of appropriate oxime concentrations. Measurements were performed at least in duplicate for each concentration tested. The oxime concentration producing 50% inhibition was determined by nonlinear fitting with ProFit (Quantumsoft) using the standard IC 50 equation: % activity=100×IC50/(IC50+[Ox]).

Reactivation of hAChE inhibited by OPNAs. The ability of the compounds to reactivate OP-inhibited hAChE were assessed with a modified Ellman assay using a microplate reader (SPARK 10M, Tecan) and a continuous method described previously [Kitz, R. J., et al. 1965, Worek, F., et al., 2004] with minor modifications. Briefly, the desired oximes concentrations to be tested were dispensed in a 96-well flat-bottomed polystyrene microplate containing 0.1% BSA phosphate buffer and DTNB. At t=0, OP-inhibited hAChE and acetylthiocholine (ATCh) diluted in 0.1% BSA phosphate buffer were injected in each well containing oximes using the built-in injectors of the microplate reader to a final volume of 200 μL. ATCh hydrolysis was continuously monitored over 30 minutes and the increase of absorbance at 412 nm recorded every 10 seconds at 25° C. Activities were individually corrected for oxime-induced hydrolysis of ATCh.

Reactivation of OP-inhibited hAChE by oximes proceeds according to scheme 6 and kinetics of oximes reactivation were determined as previously described [Worek, F., et al., 2004]. For each oxime concentration, the apparent reactivation rate, $k_{obs}$, the dissociation constant, $K_D$ and the reactivation rate constant, kr, were calculated by nonlinear fitting with ProFit (Quantumsoft) using the standard oxime-concentration-dependent reactivation equation (1):

Scheme 6

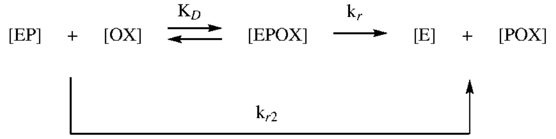

$$k_{obs} = \frac{k_r[OX]}{K_D + [OX]} \quad \text{Eq (1)}$$

When [OX]<<$K_D$, Eq (1) simplifies to Eq (2):

$$k_{obs} = \left(\frac{k_r}{K_D}\right)[OX] \quad \text{Eq (2)}$$

The second order reactivation rate constant $k_{r2}$, describing the specific reactivity can be derived from Eq (2).

$$k_{r2} = \frac{k_r}{K_D} \quad \text{Eq (3)}$$

For the continuous method of recording OP-inhibited hAChE reactivation by oximes, the velocity of substrate hydrolysis (ν) is proportional to the concentration of the reactivated hAChE and is expressed and derived as equation 4 and 5 respectively. $ν_t$ is the velocity at time t and $ν_0$ represents the maximum velocity. Equation 5 was used to determine the $k_{obs}$ by non-linear regression analysis for each individual oxime concentration with ProFit (Quantumsoft).

$$v_t = v_0\left(1 - e^{-k_{obs}t}\right) \quad \text{Eq (4)}$$

$$-d[S] = \int_0^t v\,dt = v_0 t + \frac{v_0}{k_{obs}}\left(e^{-k_{obs}t} - 1\right) \quad \text{Eq (5)}$$

The results are as follows:

TABLE 1

| Reactivation of OP-inhibited human hAChE by oximes 2-PAM, HI-6 and compounds of the invention | | | | |
|---|---|---|---|---|
| OP | Oximes | $k_r$ (min$^{-1}$) | $K_D$ (μM) | $k_{r2}$ (mM$^{-1}$ · min$^{-1}$) |
| VX | 2-PAM | 0.2 ± 0.01 | 26 ± 7 | 7 |
| | HI-6 | 0.4 ± 0.02 | 19 ± 4 | 20 |
| | JY69 | 0.4 ± 0.02 | 184 ± 24 | 2 |
| | AMI318 | 0.2 ± 0.009 | 6 ± 1.2 | 33 |
| Sarin | 2-PAM | 0.3 ± 0.02 | 25 ± 7 | 11 |
| | HI-6 | 0.8 ± 0.06 | 57 ± 11 | 13 |
| | JY69 | 0.1 ± 0.001 | 13 ± 2 | 7 |
| | AMI318 | 0.2 ± 0.004 | 1 ± 0.3 | 200 |
| Tabun | 2-PAM | 0.5 ± 0.2 | 211 ± 113 | 2 |
| | HI-6 | 0 | 0 | 0 |
| | JY69 | 0.1 ± 0.004 | 7 ± 1.5 | 16 |
| | AMI318 | 0.2 ± 0.008 | 4 ± 0.3 | 50 |
| Paraoxon | 2-PAM | 0.07 ± 0.02 | 68 ± 16 | 1 |
| | HI-6 | 0.8 ± 0.06 | 290 ± 70 | 0.4 |
| | JY69 | 0.09 ± 0.004 | 102 ± 10 | 1 |
| | AMI318 | 0.2 ± 0.006 | 2.5 ± 0.3 | 80 |

TABLE 2

| IC50 for hAChE of oximes: 2-PAM, HI-6 and compounds of the invention | |
|---|---|
| Oxime | IC50 (μM) |
| 2-PAM | 580 ± 28 |
| HI-6 | 82 ± 6 |
| JY69 | 2203 ± 196 |
| AMI318 | 156 ± 46 |

These results showed that the compounds of the invention have a broad spectrum of reactivation of OPNA-inhibited AChE: particularly they show an increased efficacy for VX and paraoxon, and a good potency against sarin.

The invention claimed is:

1. A compound, or a salt thereof, selected from the group consisting of: (Z)-6-(4-aminobutyl)-3-hydroxypicolinaldehyde oxime JY-69:

JY-69

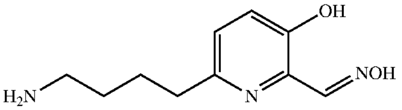

and

Tert-butyl(E)-4-(4-(5-hydroxy-6-((hydroxyimino) methyl)pyridin-2-yl)butyl)piperazine-1-carboxylate AMI 318:

AMI 318

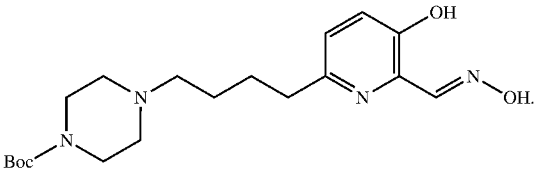

2. A pharmaceutical composition comprising at least one compound according to claim 1, and at least one pharmaceutically acceptable excipient, disintegrant, binder, lubricant, flavorant, colorant, stabilizer, or thickener.

3. A method for treating a subject in need thereof, comprising administering to said subject at least one compound according to claim 1.

4. A method for treating a nervous and/or respiratory failure due to intoxication with at least one organophosphorous nerve agent, by virtue of their reactivation potency of organophosphorous inhibited cholinesterases, in a subject in need thereof, comprising administering to said subject at least one compound according to claim 1.

5. A method for treating a neurological disease in a subject in need thereof, comprising administering to said subject at least one compound according to claim 1.

6. A method for treating cancer in a subject in need thereof, comprising administering to said subject at least one compound according to claim 1.

7. The compound, or salt thereof, of claim 1 wherein the compound is (Z)-6-(4-aminobutyl)-3-hydroxypicolinaldehyde oxime JY-69

JY-69

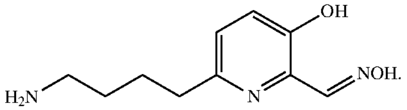

8. The compound, or salt thereof, of claim 1 wherein the compound is Tert-butyl(E)-4-(4-(5-hydroxy-6-((hydroxyimino)methyl)pyridin-2-yl)butyl)piperazine-1-carboxylate AMI 318

AMI 316

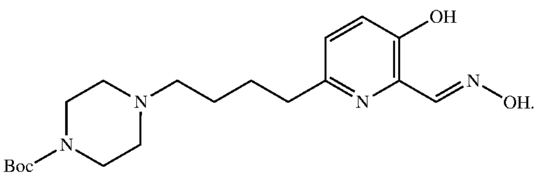

9. The compound, or salt thereof, of claim 1 wherein the compound is formed as a hydrochloride salt.

* * * * *